United States Patent [19]

Fischer

[11] Patent Number: 5,289,919
[45] Date of Patent: Mar. 1, 1994

[54] ENDODONTIC DENTAL KIT WITH COLOR-CODING MEANS

[75] Inventor: Dan E. Fischer, Sandy, Utah

[73] Assignee: Ultradent Products, Inc., South Jordan, Utah

[21] Appl. No.: 18,096

[22] Filed: Feb. 16, 1993

[51] Int. Cl.⁵ .................. B65D 83/02; B65D 71/00
[52] U.S. Cl. .................... 206/571; 206/63.5; 206/366; 206/369; 206/459.5; 433/77; 433/147
[58] Field of Search ............... 206/365–370, 206/571, 459.5, 63.5; 433/77, 79, 146, 147

[56] References Cited

U.S. PATENT DOCUMENTS

| | | | |
|---|---|---|---|
| 611,136 | 9/1898 | Mason | 206/459.5 X |
| 2,214,230 | 9/1940 | Freeburg | 206/459.5 X |
| 2,557,222 | 6/1951 | Goode | 206/365 |
| 2,929,510 | 3/1960 | Penn | 206/366 X |
| 2,985,285 | 5/1961 | Riddle | 206/366 |
| 4,353,694 | 10/1982 | Pelerin | 206/369 X |
| 4,552,531 | 11/1985 | Martin | 433/147 |

*Primary Examiner*—Bryon P. Gehman
*Attorney, Agent, or Firm*—Workman Nydegger Jensen

[57] ABSTRACT

A kit for assembling a variety of dental devices using a plurality of delivery tips that differ from one another as to either size or type. The kit also includes a plurality of differently sized syringes each being releasably attachable to any one of the plurality of delivery tips. An organizer displays the syringes and delivery tips in such way that the size and type of syringe and delivery tip desired is easily identifiable. The kit may include adapters which connect any of the plurality of delivery tips to either a vacuum source or to an air bulb. The delivery tips may be color coded such that the size and type of delivery tip is indicated by the color code of the delivery tip.

25 Claims, 5 Drawing Sheets

ENDODONTIC DENTAL KIT WITH COLOR-CODING MEANS

BACKGROUND

1. Field of the Invention

The present invention is related to kits for assembling various dental devices. More particularly, the present invention is related to kits for assembling various dental devices wherein different sizes of syringes, delivery tips, and other dental components are coordinated and readily available to be combined for different uses.

2. Prior State of the Art

A wide variety of different types of dental equipment is used in today's dental practice. For best results, a particular size and type of device is used for each different process. For example, one type of syringe may be needed for irrigation of the teeth, while another type of syringe may be needed for expressing material such as a bonding agent onto teeth surfaces. When several procedures are used in one sitting, many different devices may be needed.

Unfortunately, trying to assemble and keep together all the various devices that may be needed in one compact area is often frustrating and very time consuming. The various pieces are usually not organized in a convenient fashion, and the dentist is not always able to obtain each desired piece of equipment quickly and easily. It is often difficult for the dentist to be able to instantly identify from his supply of equipment the correct size and type of device needed, and then be able to conveniently obtain the correct device once it is identified.

BRIEF SUMMARY AND PRINCIPAL OBJECTS OF THE INVENTION

The present invention seeks to resolve the problems which have been experienced in the art. More particularly, the kit of this invention constitutes an advancement in organization of dental equipment in a compact, convenient manner, as evidenced by the following principal objects and advantages realized by the invention over the prior art.

One object of the present invention is to provide a kit for assembly of dental devices wherein different sizes of syringes and delivery tips are organized for easy accessibility.

Another object of the present invention is to provide a kit for assembly of dental devices wherein differently sized delivery tips are readily identifiable and accessible.

An additional object of the present invention is to provide a kit for assembly of dental devices wherein different sizes of syringes and delivery tips are organized in one carrier so that many different combinations of syringes and delivery tips can be easily made using the components within the carrier.

Still another object of the present invention is to provide a kit for assembly of dental devices wherein the various sizes and types of delivery tips are color coded for quick identification.

Yet another object of the present invention is to provide a kit for assembly of dental devices wherein some of the various components may be assembled to allow connection to a vacuum source and to allow suction through a wide variety of delivery tips of different sizes and types.

Further, an object of the present invention is to provide a kit for assembly of dental devices wherein some of the various components may be assembled to allow aeration of the teeth for purposes of drying through a wide variety of delivery tips of different sizes and types.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, the present invention comprises a kit for assembling a variety of dental devices using a plurality of delivery tips that differ from one another as to either size or type.

In one presently preferred embodiment of the kit of the present invention, the kit comprises a plurality of syringes of different sizes, each differently sized syringe being adapted for a different use. The kit also comprises a plurality of delivery tips of different sizes and types, and an organizer for holding each of the plurality of syringes and delivery tips using a color coded display.

Any of the plurality of delivery tips can be removably attached to any of the differently sized syringes, depending upon the size and type of syringe and delivery tip desired. In one presently preferred embodiment, the plurality of delivery tips are color coded such that the size and type of the delivery tips are indicated by their color. Each different size and type of delivery tip is indicated by a different color. All delivery tips of the same size or of the same type have the same color. Therefore, easy and quick visual identification of the particular size or type of delivery tips is provided.

In the preferred embodiment of the present invention, each different size and type of delivery tip may be housed in separate containers. Each container may also be colored to match the color of the delivery tips contained therein, further enhancing visual identification of each type and size.

In another embodiment of the present invention, the kit also includes an adaptor which allows the different delivery tips to be connected to a vacuum source such that suction can be provided through any of the delivery tips. The kit may also include an adaptor which allows the different delivery tips to be connected to an air bulb. Squeezing the air bulb allows aeration to be provided to the teeth through any of the different delivery tips. The kit of the present invention organizes and holds all components together in one easily accessible display.

BRIEF DESCRIPTION OF THE DRAWINGS

In order to more fully understand the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention in its presently understood best mode for making and using the same will be described with additional specificity and detail through the use of the accompanying drawings in which.

DETAILED DESCRIPTION OF THE PREFERRED EMBODIMENTS

Figure 1:
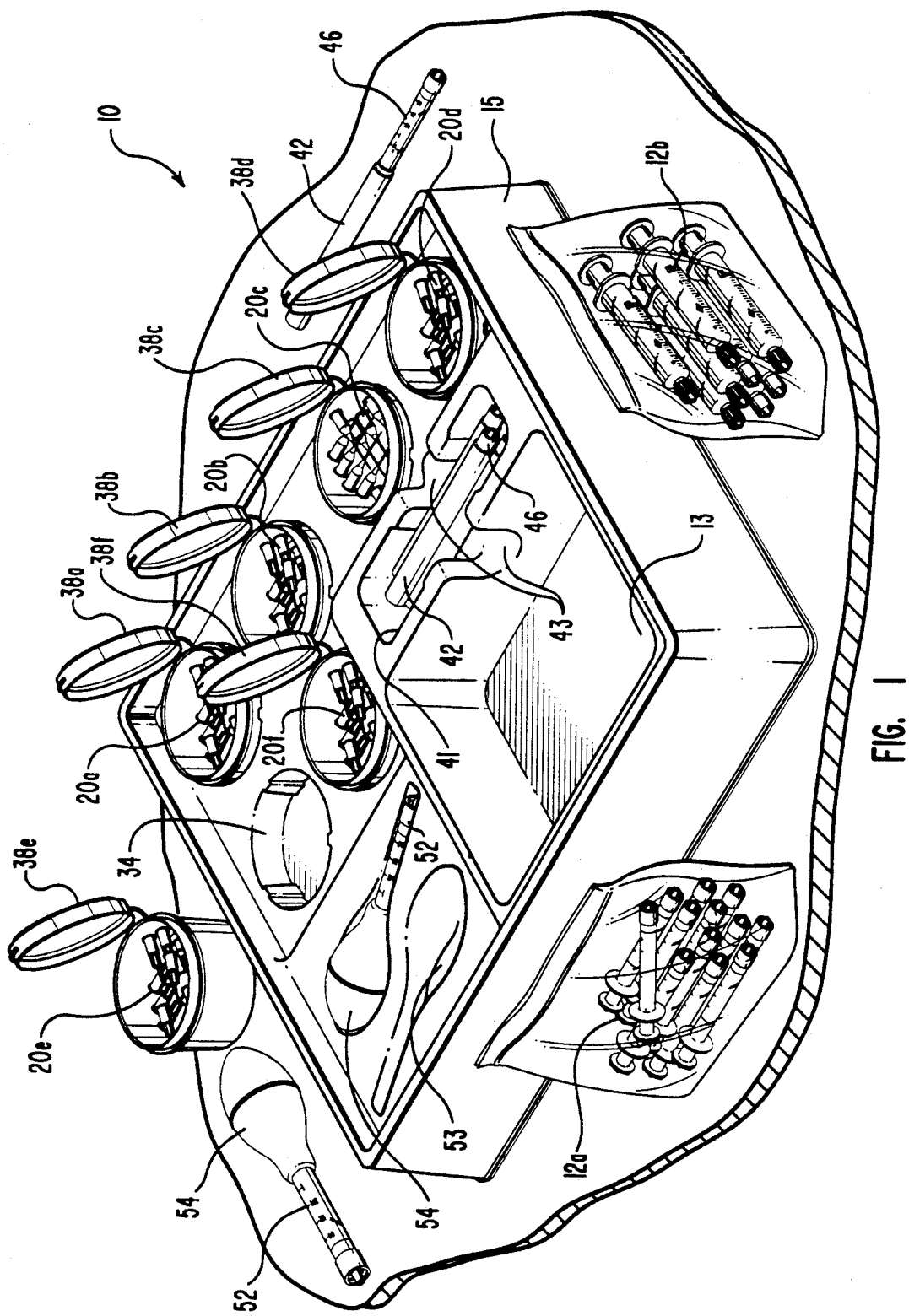
FIG. 1 is a perspective view of the preferred embodiment of the kit of the present invention, wherein the various components of the kit are displayed both seated within and to the side of the kit.

Reference is now made to the drawings wherein like parts are designated with like numerals throughout. Referring first to FIG. 1, one presently preferred embodiment of the kit of the present invention is illustrated and generally designated 10.

In one aspect of the present invention, kit 10 comprises a plurality of components organized into one compact unit. As hereinafter more fully described, the plurality of components can be connected together in various combinations in order to form different devices to be used for different purposes. The components are displayed such that the desired size and/or type of component can be easily differentiated and chosen.

Figure 2:
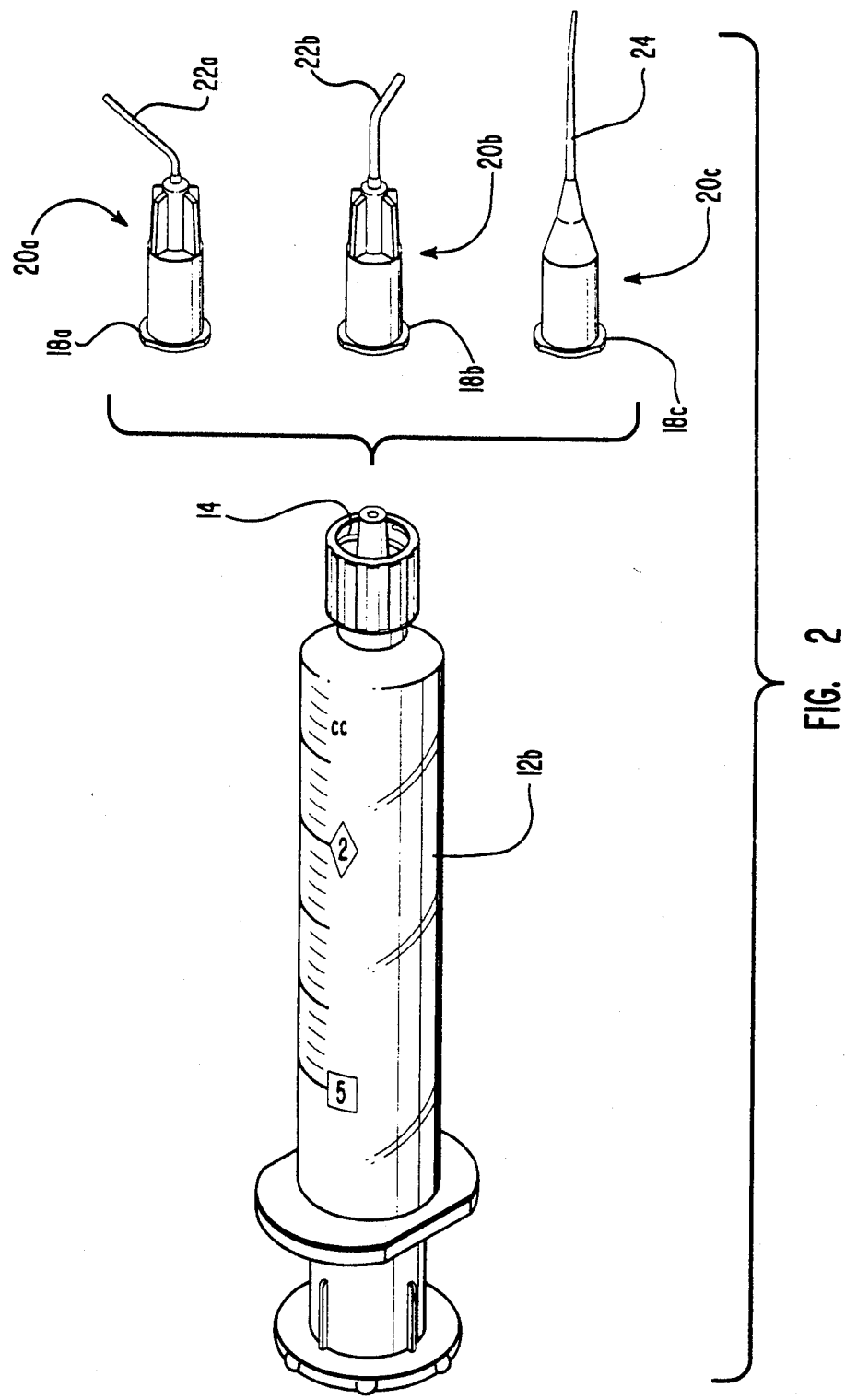
FIG. 2 is a perspective view of a large syringe capable of being attached to any one of a plurality of delivery tips that differ as to size and/or type.

One type of component included in the kit 10 is a plurality of differently sized syringes 12a-12b. Each differently sized syringe 12a-12b is adapted for a different use. As shown in FIG. 2, in the presently preferred embodiment, each syringe 12 is comprised of an end 14 with a connector means for attachment to a delivery tip. In the presently preferred embodiment, the connector means comprises a luer lock female connector 14 to which a delivery tip may be connected. Three different types of delivery tips are shown as examples of tips connectable with luer lock female connector 14.

Figure 3:
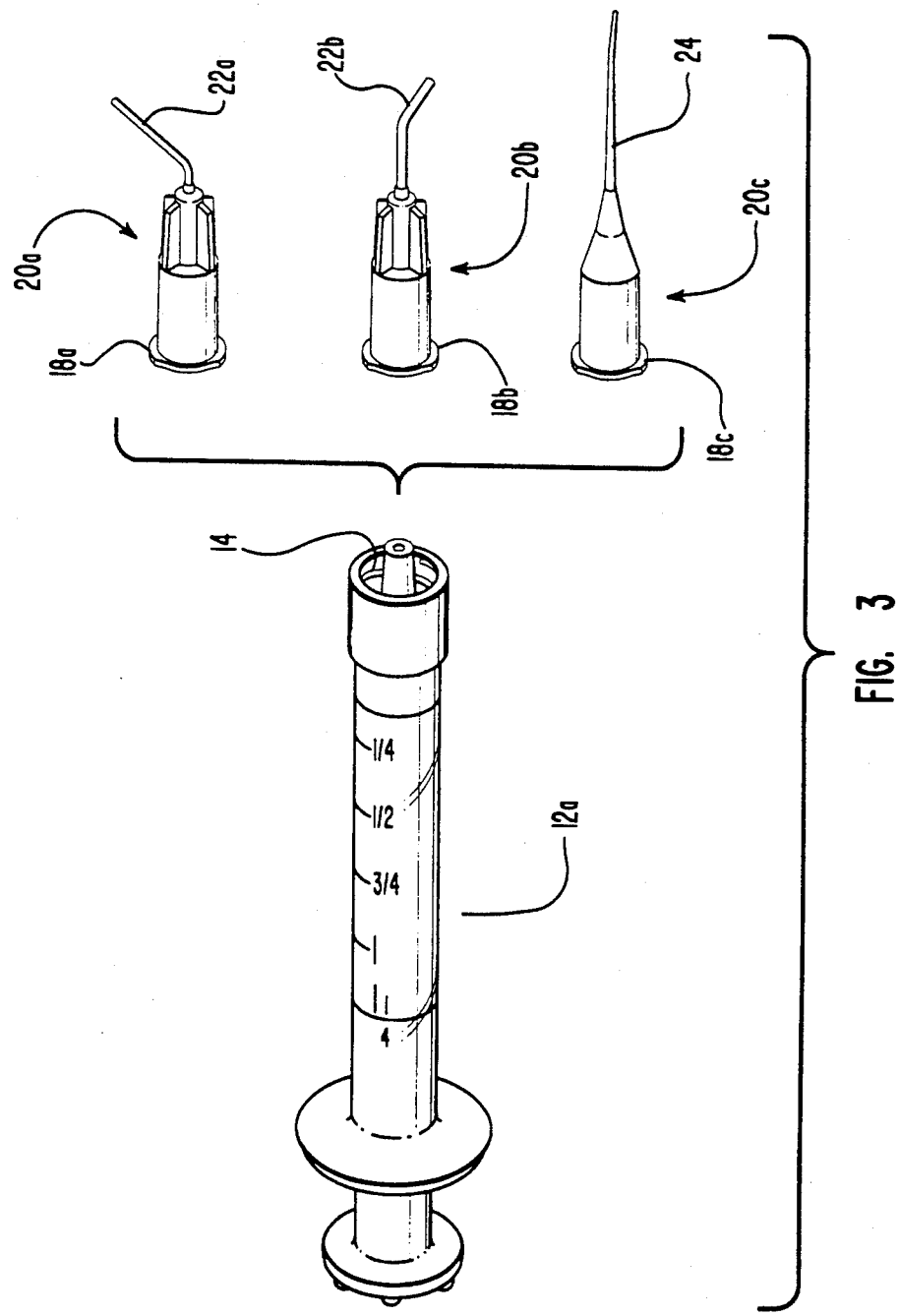
FIG. 3 is a perspective view of a small syringe capable of being attached to any one of a plurality of delivery tips that differ as to size and/or type.

In FIG. 3, a differently sized syringe 12a having the same luer lock female connector 14 is illustrated. Both sizes of syringes are capable of being attached to any of the various sizes of delivery tips 20.

Kit 10 may also comprise a plurality of delivery tips 20a-20f of different sizes and/or types. Each delivery tip 20 comprises a hub means for providing releasable attachment to the connector 14 of any syringe 12a-12b. In the presently preferred embodiment, the hub means comprises a luer lock male connector 18 which is insertable into the luer lock female connector 14 for a secure fit. Any of the different sizes and/or types of delivery tips 20a-20f are releasably connectable to any of the different sizes and types of syringes 12a-12b. The hub 18 of the delivery tips 20a-20f are preferably comprised of a medical grade plastic material.

Each delivery tip 20a-20f also comprises a delivery end. The delivery ends of at least some of the delivery tips 20 differ from one another as to either size or type. Some of the delivery ends comprise a non-tapered, deformable metal cannula 22 which can be bent or shaped as desired, as shown for example in FIG. 2 at 22a and 22b.

The non-tapered deformable cannulae 22 are available in various different sizes, as also depicted at 22a and 22b. Preferably, the non-tapered deformable cannulae 22 are comprised of a dead soft metal material. Other soft, deformable materials are also within the scope of the present invention.

Some of the delivery ends comprise a long, tapered flexible and resilient cannulae 24. In the preferred embodiment, only one size of tapered flexible cannula 24 is shown. However, it can be appreciated that various sizes of cannulae 24 may also be included within the kit. It is preferred that tapered flexible cannula 24 be comprised of a medical grade, resilient plastic material.

In use, it is desired that the size and/or type of delivery tip 20a-20f be easily identifiable. Therefore, in the presently preferred embodiment of the present invention, the hub 18 of each delivery tip 20a-20f is comprised of a color-coded means for identifying the size or type of delivery cannula 22 or 24. Specifically, each differently sized delivery tip 22a-22b comprises a differently colored hub 18a-18b. Delivery tips of the same size and/or type all have the same colored hub 18. Delivery tips of different sizes and/or types have differently colored hubs 18. Thus, the size and/or type of delivery tip can be quickly and easily identified and chosen by visualizing the particular corresponding color of hub.

A third component of kit 10 of the present invention is an organizing means for holding each of the plurality of syringes 12 and delivery tips 20. The organizing means is preferably comprised of a unitary tray 15 that holds each of the plurality of syringes 12 and delivery tips 20 in a manner such that the color-coded hub 18 of each delivery tip 20 is readily observable and distinguishable. This permits the different delivery tips 20a-20f to be quickly and easily differentiated and selected based on the size or type of cannula 22 or 24 desired.

Referring back to the preferred embodiment of FIG. 1, the organizing tray 15 may comprise a plurality of integrally formed receptacles 34, 41, 43 and 53 for receiving therein the plurality of components. Each receptacle separately holds one type of component.

The plurality of receptacles may be comprised of a plurality of wells 34 positioned adjacent each other, such that when the differently sized delivery tips 20a-20f are contained therein, the color coded hubs 18 are displayed so as to provide ready identification of the size and/or type of delivery tip 20 contained therein.

The organizing tray 15 may also hold a plurality of canisters 38a-38f. Each canister 38 holds therein a plurality of the delivery tips 20 of a specific size or type. Each canister 38 preferably is comprised of a color which matches the color of the hub 18 of the delivery tips 20 contained therein. This color coordination assures easy identification of the size and/or type of the delivery tip 20 desired. The plurality of canisters 38 may be fit within and securely received within the plurality of adjacent wells 34.

Figure 4:
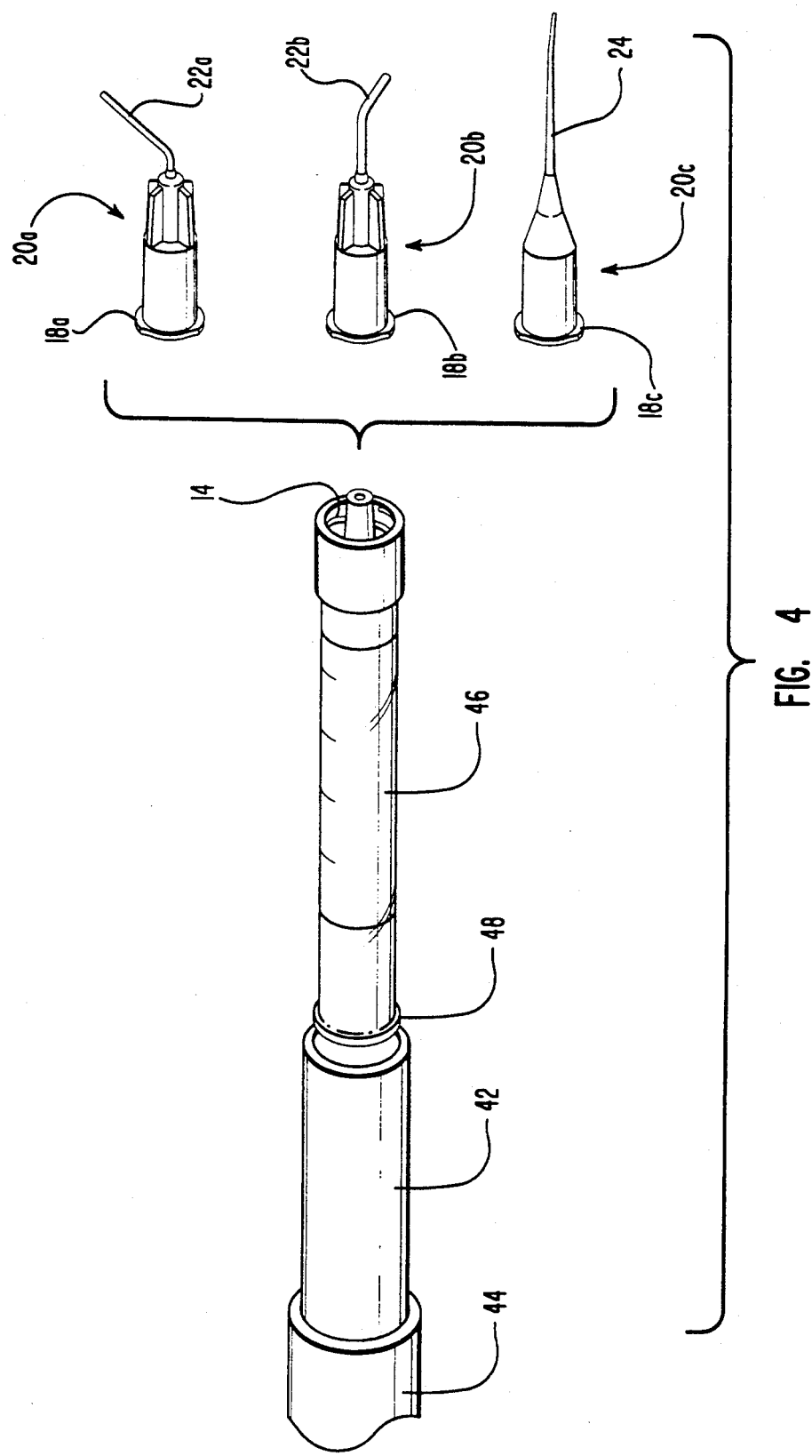
FIG. 4 is an exploded perspective view of a an adapter which is connectable to a vacuum source and to any of the various delivery tips.

FIG. 4 illustrates a fourth component which may be included within kit 10. This fourth component comprises a first adaptor means for connection of any one of the plurality of different delivery tips to a vacuum source, so as to provide suction through any one of the delivery tips so connected. The first adaptor means comprises a cylindrical sleeve 42 which is connectable to a vacuum source 44. An elongated connecting member 46 is longitudinally slidable within cylindrical sleeve 42, such that a telescoping effect between connecting member 46 and cylindrical sleeve 42 is created.

Connecting member 46 is connectable at one end to any one of the delivery tips 20. At the other end, connecting member 46 has a rim 48 around the circumference of the end. Rim 48 provides essentially a fluid tight, slidable fit with connecting member 46 from within cylindrical sleeve 42. Also, as connecting member 46 slides outward within the cylindrical sleeve 42, rim 48 tends to prevent connecting member 46 from being accidentally removed from cylindrical sleeve 42.

Any of the different sizes or types of delivery tips 20a–20f can be connected to the end of connecting member 46 through a luer lock female connector 14 located on the end of each connecting member 46, which is engageable with the hub 18 of any the delivery tips 20a–20f. Thus, suction may be provided through any size or type of delivery tip 20a–20f available for connection with connecting member 46.

Figure 5:
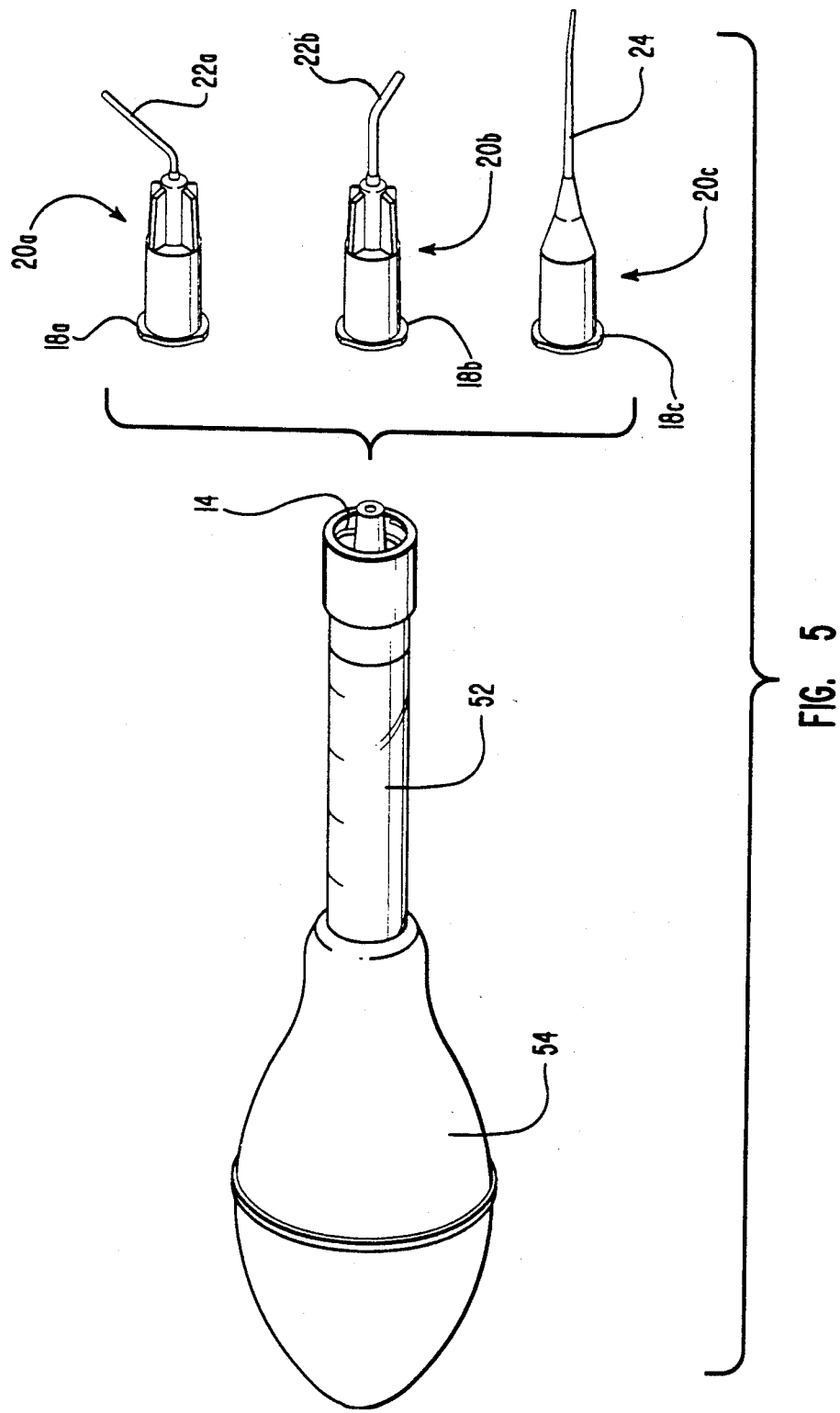
FIG. 5 is an exploded view of another adapter which is connectable to any of the various delivery tips for purposes of providing aeration.

Illustrated in the exploded view of FIG. 5 is a second adaptor means for connecting any one of the plurality of different delivery tips 20a–20f to an air bulb. The second adaptor means provides aeration for purposes of drying, through any one of the plurality of delivery tips 20a–20f.

In the preferred embodiment within the scope of the present invention, the second adaptor means comprises an elongated connecting member 52 which is essentially identical to member 46 described above, and which is connectable at one end to any one of the plurality of different delivery tips 20a–20f, and connectable at the other end to an air bulb 54. In use, squeezing the air bulb 54 causes air to be forced through elongated connecting member 52 and through the connected delivery tip 20. A luer lock female connector 14, such as is present on the first adaptor 42 and the plurality of syringes 12, is also present at the end of elongated connecting member 52 so that any of the plurality of delivery tips 20a–20f can be connected thereto.

USE OF THE KIT

The kit of the present invention is used for assembling a variety of dental devices using a plurality of delivery tips that differ from one another as to either size or type. The kit may be used to assemble many types of devices. For example, the kit may be used to assemble any one or all of the following: a syringe 12 of any size having connected thereto a delivery tip 20 having a non-tapered deformable cannula 22 with a selected size cannula; a syringe 12 of any size having connected thereto a delivery tip 20 having a tapered, flexible cannula 24; an adaptor 42 connected at one end to a source of vacuum and connected at the other end to a delivery tip 20 having a non-tapered deformable cannula 22 with a selected size cannula; an adaptor 42 connected at one end to a source of vacuum and connected at the other end to a delivery tip having a tapered flexible cannula 24; an adaptor 52 connected at one end to an air bulb 54 and at the other end to a delivery tip 20 having a non-tapered deformable cannula 22 with a selected size cannula; or an adaptor 52 connected at one end to an air bulb 54 and at the other end to a delivery tip 20 having a tapered flexible cannula 24. Each of these devices can be used for different purposes.

To use the kit, a delivery tip 20 of appropriate size and type is selected and attached to the air bulb adaptor 52, the vacuum adaptor 42, or an appropriately sized syringe 12a–12b as required for drying, vacuuming, or delivering solutions, cements, composites, etc. to the teeth. Some typical examples of use of the devices assembled by the kit are described below.

For instance, in order to irrigate a tooth with disinfecting solution such as sodium hypochlorite, the kit may be used to quickly assemble a large syringe 12b (see FIG. 2) having connected thereto either a tapered flexible plastic delivery tip 20c, or a delivery tip 20a having a 27 gauge. When color coded hubs 18 are present on the delivery tips 20, it is easy and convenient for the user to be able to quickly identify the size or type of delivery tip 20 desired. The user simply chooses the tip with the color corresponding to the size and type of cannula desired.

By attaching a 22 gauge non-tapered bendable delivery tip 20b (see FIG. 4) to the first adaptor 42, and then connecting the first adaptor 42 to a vacuum source 44, debris from the canal of a tooth can be removed by suction. This procedure greatly minimizes the number of paper points usually required for drying such a canal.

If further drying is desired, the second adaptor 52 (see FIG. 5) that is connected to the air bulb 54 on one end, may be attached on the other end to any deformable tip 20a–20b or to the tapered flexible tip 20c. Squeezing the air bulb 54 provides a passive air source to accomplish further drying of the tooth canal.

If bonding to dentin of a post hole, primers are inserted into a small syringe 12a such as a 1.2 cc syringe (see FIG. 3). The syringe is inverted a few time to mix the primers. A 22 gauge tip 20b is attached to the syringe 12a and the mixed primers are delivered to the bottom of a plurality of post holes prepared in the canal. An air bulb 54 connected to the second adapter 52 along with a 20 gauge tip 20 is then used to puff out excess primer between each coat. Bonding resin is applied to the bottom of the post hole through an appropriately sized and appropriate type of tip and excess is blown out with a tip attached to an air bulb. Post holes should be filled with resin using a tip having the largest diameter available so that it can slide easily to the bottom of the post hole and be loose enough to provide an escape for excess luting resin. Posts are then inserted following luting resin delivery. If cements are used rather than resin dentin bonding technology, the cements are mixed, delivered to a small syringe and expressed to the post hole as described above for luting resin.

A small syringe 12a and a 20 gauge tip 20 can be used to deliver sealing material. Irrigation of potential pockets, fistulas, etc. with appropriate solutions such as diluted hydrogen peroxide, or saline solution, can be accomplished using the small tapered flexible plastic tip 20.

It can be appreciated that many combinations of the components can be used for different purposes. In the embodiments having the color coded identification system, the size and/or type of delivery tip desired can be easily selected through selection of the appropriate color. Where canisters similarly colored are used, location of the correct canister holding the desired delivery tips is quick, easy, and convenient.

It should be appreciated that the kit of the present invention provides for the assembly of the many devices from one small compact container. Only a small amount of counter space is used, thereby freeing the counter space for other dental equipment. Additionally, the kit is portable and is easily moved from station to station. Further, the kit can be refilled at any time, therefore allowing the kit to be reused indefinitely. Through use of the kit of the present invention, a dentist can be more efficient and organized, and can change devices for each different procedure easily and immediately.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States patent is:

1. A kit for assembling a variety of dental devices using a plurality of delivery tips that differ from one another as to either size or type, said kit comprising:
   (a) a plurality of syringes of different sizes, each differently sized syringe being adapted for a different use, and each syringe having an end with a connector means for attaching said syringe to any of a plurality of delivery tips;
   (b) a plurality of delivery tips each comprising a hub means for providing releasable attachment of one of said delivery tips to said connector means of any syringe, and each of said delivery tips having a delivery end, wherein the delivery end of at least some of the delivery tips differ from one another as to either size or type, some of said delivery ends comprising a non-tapered, deformable cannula with at least some of the deformable cannulae differing in size, and some of said delivery ends comprising a tapered flexible cannula, and wherein the hub means of each said delivery tip is comprised of a color-coded means for identifying the size or type of delivery cannula;
   (c) organizing means for holding each of said pluralities of syringes and delivery tips in a manner such that the color-coded means of each delivery tip is readily distinguishable to permit the different delivery tips to be quickly and easily differentiated and selected based on the size or type of cannula desired; and
   (d) wherein the organizing means comprises a plurality of canisters for holding the plurality of differently sized delivery tips, each canister holding therein delivery tips of a size different from delivery tips held within other canisters, and all of the delivery tips within each single canister being of the same size, and each canister being comprised of a color which matches the color-coded means on the hub means of the delivery tips contained within the canister, thereby assuring color coordinated identification of the size and type of the delivery tips contained within each canister.

2. A kit as defined in claim 1, wherein the non-tapered, deformable cannulae are comprised of deformable metal.

3. A kit as defined in claim 1, wherein the tapered flexible cannulae are comprised of a medical grade, resilient plastic material.

4. A kit as defined in claim 1, wherein the hub means is comprised of a medical grade plastic material which is tinted with a color for identifying the size or type of delivery cannula.

5. A kit as defined in claim 1, wherein the connector means comprise a luer lock connector with which the hub means of the delivery tips can be releasably attached.

6. A kit as defined in claim 5, wherein the hub means comprises a luer lock connector.

7. A kit as defined in claim 1, wherein the organizing means further comprises a unitary tray having a plurality of integrally formed receptacles for receiving therein the pluralities of syringes and delivery tips.

8. A kit as defined in claim 7, wherein each differently sized plurality of syringes and delivery tips is received within a separate integrally formed receptacle.

9. A kit as defined in claim 1, wherein the organization means further comprises a plurality of walls positioned adjacent each other for holding the delivery tips of different sizes and types, such that the color coded means provides ready identification when a plurality of said delivery tips are in separate wells.

10. A kit as defined in claim 1, wherein the kit further comprises a first adaptor means for connecting any one of the plurality of different delivery tips to a vacuum source so as to provide suction through any one of the delivery tips so connected.

11. A kit as defined in claim 10, wherein the first adaptor means comprises a cylindrical sleeve which is connectable to a vacuum source, and an elongated connecting member longitudinally slidable within said cylindrical sleeve, said elongated connecting member being connectable at one end to any one of said delivery tips.

12. A kit as defined in claim 1, further comprising a second adaptor means for connecting any one of the plurality of different delivery tips to an air bulb so as to provide aeration for purposes of drying through any one of the delivery tips so connected.

13. A kit as defined in claim 12, wherein the second adaptor means comprises an elongated connecting member which is connectable at one end to any one of the plurality of different delivery tips and connectable at the other end to an air bulb.

14. A kit for assembling a variety of dental devices using a plurality of delivery tips that differ from one another as to either size or type, said kit comprising:
   (a) a plurality of syringes of different sizes, each differently sized syringe being adapted for a different use, and each syringe having an end with a connector means for attaching the syringe to any of a plurality of delivery tips;
   (b) a plurality of delivery tips each comprising a hub means for providing releasable attachment of one of the delivery tips to said connector means of any syringe, and each of said delivery tips having a delivery end, and wherein the delivery ends of at least some of the delivery tips differ from one another as to either size or type, some of said delivery ends comprising a non-tapered, deformable cannula with at least some of the deformable cannulae differing in size, and some of said delivery ends comprising a tapered flexible cannula, and wherein the hub means of each said delivery tip is comprised of a color-coded means for identifying the size or type of delivery cannula;
   (c) first adaptor means for connecting any one of the plurality of different delivery tips to a vacuum source so as to provide suction through any one of the delivery tips so connected;
   (d) second adaptor means for connecting any one of the plurality of different delivery tips to an air bulb so as to provide aeration for purposes of drying through any one of the delivery tips so connected; and (e) organizing means for holding each of said pluralities of syringes, delivery tips, first adaptor means, and second adaptor means in a manner such that the color-coded means of each delivery tip is readily distinguishable to permit the different delivery tips to be quickly and easily differentiated and selected based on the size or type of cannula desired;

(f) wherein the organization means further comprises a plurality of wells positioned adjacent each other for holding the delivery tips of different sizes and types, such that the color coded means provides ready identification when a plurality of said delivery tips are in separate wells;

(g) wherein the organizing means is further comprised of a tray having a plurality of integrally formed receptacles for receiving therein the pluralities of syringes and delivery tips;

(h) wherein each of said differently sized pluralities of syringes and delivery tips is received within a separate integrally formed receptacle; and (i) wherein said kit further comprises a plurality of canisters, each canister holding therein a plurality of said delivery tips, all of the delivery tips within each canister being the same size, and each canister being comprised of a color which matches the color of the color-coded means of the delivery tips contained therein, thereby assuring color coordinated identification of the size and type of the delivery tips contained therein.

15. A kit as defined in claim 14, wherein the non-tapered, deformable cannulae are comprised of deformable metal.

16. A kit as defined in claim 15, wherein the tapered flexible cannulae are comprised of a medical grade, resilient plastic material.

17. A kit as defined in claim 16, wherein the hub means is comprised of a medical grade plastic material.

18. A kit for assembling a variety of dental devices using a plurality of delivery tips that differ from one another as to either size or type, said kit comprising:
 (a) a plurality of differently sized syringes, each differently sized syringe being adapted for a different use, each syringe having an end with a connector means for attaching the syringe to any one of a plurality of different delivery tips;
 (b) first adaptor means for connecting any one of a plurality of different delivery tips to a vacuum source so as to provide suction through any one of the delivery tips so connected;
 (c) second adaptor means for connecting any one of a plurality of different delivery tips to an air bulb so as to provide aeration for purposes of drying through any one of the delivery tips so connected;
 (d) a plurality of delivery tips that differ from one another as to either size or type, each said delivery tip comprising a hub means for providing releasable attachment of the delivery tips to the connector means of a syringe or to one said adaptor means, each of said delivery tips further comprising a delivery end and wherein the delivery ends of at least some of the delivery tips differ from one another as to either size or type, some of said delivery ends comprising a non-tapered, deformable cannula with at least some of the deformable cannulae differing in size, and some of said delivery ends comprising a tapered flexible cannula;

(e) organizing means for holding each of said pluralities of syringes, adaptor means and delivery tips separate from one another, the organizing means comprising a plurality of canisters for holding the plurality of said differently sized delivery tips, each canister holding therein delivery tips of a size different from delivery tips held within other canisters, and all of the delivery tips within each single canister being of the same size, and each canister being comprised of a color which matches the color-coded means on the hub means of the delivery tips contained within the canister, thereby assuring color coordinated identification of the size and type of the delivery tips contained within each canister; and (f) whereby said kit can be used to assemble any one or all of the following dental devices;
 (1) a syringe of any size having connected thereto a delivery tip having a non-tapered deformable cannula with a selected size cannula;
 (2) a syringe of any size having connected thereto a delivery tip having a tapered, flexible cannula;
 (3) a first adaptor means connected at one end to a source of vacuum and connected at the other end to a delivery tip having a non-tapered deformable cannula with a selected size cannula;
 (4) a first adaptor means connected at one end to a source of vacuum and connected at the other end to a delivery tip having a tapered flexible cannula;
 (5) a second adaptor means connected at one end to an air bulb and at the other end to a delivery tip having a non-tapered deformable cannula with a selected size cannula; and
 (6) a second adaptor means connected at one end to an air bulb and at the other end to a delivery tip having a tapered flexible cannula.

19. A kit as defined in claim 18, wherein the organization means further comprises a plurality of wells positioned adjacent each other for holding the delivery tips of different sizes and types, such that the color coded means provides ready identification when a plurality of said delivery tips are in separate wells, said wells being sized so as to securely receive said colored canisters therein.

20. A kit as defined in claim 18, wherein the non-tapered, deformable cannulae are comprised of metal.

21. A kit as defined in claim 18, wherein the tapered flexible cannulae are comprised of a medical grade, resilient plastic material.

22. A kit as defined in claim 18, wherein the hub means is comprised of a medical grade plastic material.

23. A kit as defined in claim 18, wherein the connector means comprise a luer lock connector into which the hub means of the delivery tips can releasably attach.

24. A kit as defined in claim 23, wherein the hub means comprises a luer lock connector.

25. A kit for assembling a variety of dental devices using a plurality of delivery tips that differ from one another as to either size or type, said kit comprising:
 (a) a plurality of differently sized syringes, each differently sized syringe being adapted for a different use, each syringe having an end with a connector means for attaching the syringe to any one of a plurality of different delivery tips;
 (b) first adaptor means for connecting any one of a plurality of different delivery tips to a vacuum source so as to provide suction through any one of the delivery tips so connected;

(c) second adaptor means for connecting any one of a plurality of different delivery tips to an air bulb so as to provide aeration for purposes of drying through any one of the delivery tips so connected;

(d) a plurality of delivery tips that differ from one another as to either size or type, each said delivery tip comprising a hub means for providing releasable attachment of the delivery tips to the connector means of a syringe or to one said adaptor means, each of said delivery tips further comprising a delivery end and wherein the delivery end of at least some of the delivery tips differ from one another as to either size or type, some of said delivery ends comprising a non-tapered, deformable cannula with at least some of the deformable cannulae differing in size, and some of said delivery ends comprising a tapered flexible cannula, and wherein the hub means of each said delivery tip is comprised of a specific color which identifies the size or type of delivery cannula;

(e) organizing means for holding each of said pluralities of syringes, adaptor means and delivery tips separated from one another and in a manner such that the colored hub means of each delivery tip is readily distinguishable to permit the different delivery tips to be quickly and easily differentiated and selected based on the size or type of cannula desired, said organizing means comprising a tray having therein separate integrally formed compartments for holding the plurality of differently sized syringes, adaptor means and delivery tips, and further comprising a plurality of canisters, each canister containing therein a plurality of said delivery tips having different sizes, all of the delivery tips within each separate canister being the same size, and each canister being comprised of a color which matches the color of the hub means of the delivery tips contained therein; and (f) whereby said kit can be used to assemble any one of the following dental devices;
   (1) a syringe of any size having connected thereto a delivery tip having a non-tapered deformable cannula with a selected size cannula;
   (2) a syringe of any size having connected thereto a delivery tip having a tapered, flexible cannula;
   (3) a first adaptor means connected at one end to a source of vacuum and connected at the other end to a delivery tip having a non-tapered deformable cannula with a selected size cannula;
   (4) a first adaptor means connected at one end to a source of vacuum and connected at the other end to a delivery tip having a tapered flexible cannula;
   (5) a second adaptor means connected at one end to an air bulb and at the other end to a delivery tip having a non-tapered deformable cannula with a selected size cannula; and
   (6) a second adaptor means connected at one end to an air bulb and at the other end to a delivery tip having a tapered flexible cannula.

* * * * *

UNITED STATES PATENT AND TRADEMARK OFFICE
CERTIFICATE OF CORRECTION

PATENT NO. : 5,289,919
DATED : March 1, 1994
INVENTOR(S) : DAN E. FISCHER

It is certified that error appears in the above-identified patent and that said Letters Patent is hereby corrected as shown below:

Title page, Abstract, line 8, before "way" insert --a--
Column 6, line 28, "time" should be --times--

Signed and Sealed this

Third Day of February, 1998

Attest:

BRUCE LEHMAN

Attesting Officer

Commissioner of Patents and Trademarks